(12) United States Patent
Gan et al.

(10) Patent No.: US 6,388,170 B1
(45) Date of Patent: May 14, 2002

(54) BIDIRECTIONAL PROMOTERS AND METHODS RELATED THERETO

(75) Inventors: Susheng Gan, Lexington, KY (US); Mingtang Xie, Burnaby (CA); Yuehui He, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/545,244

(22) Filed: Apr. 7, 2000

(51) Int. Cl.[7] ........................... C12Q 1/68; C12P 19/34; C12N 15/64; C07H 21/04; A01H 1/00
(52) U.S. Cl. ..................... 800/278; 435/6; 435/91.1; 435/91.4; 435/468; 536/23.1; 536/24.1; 800/298
(58) Field of Search .................... 435/6, 69.1, 69.2, 435/91.1, 455, 468, 471, 375, 410, 320.1; 536/23.1, 24.1, 25.3

(56) References Cited

U.S. PATENT DOCUMENTS

| | | | |
|---|---|---|---|
| 5,359,142 A | 10/1994 | McPherson et al. | 800/205 |
| 5,368,855 A | 11/1994 | Boyle et al. | 435/320.1 |
| 5,424,200 A * | 6/1995 | McPherson et al. | 435/70.1 |
| 5,627,046 A | 5/1997 | Falcone et al. | 435/69.1 |
| 5,814,618 A | 9/1998 | Bujard et al. | 514/44 |
| 5,827,693 A | 10/1998 | De Angelo et al. | 435/69.6 |
| 5,837,849 A * | 11/1998 | Ellis et al. | 536/24.1 |
| 5,955,646 A | 9/1999 | Gelvin et al. | 800/205 |
| 6,004,941 A * | 12/1999 | Bujard et al. | 514/44 |

OTHER PUBLICATIONS

Udo Baron et al., Co–regulation of two gene activities by tetracycline via a bidirectional promoter, Nucleic Acids Research, vol. 23, No. 17, 1995 pp. 3605–3606.*
Odell, et al., 313 *Nature* 810 (1985).
Benfey, et al., 250 *Science* 959 (1990).
Lewin, B., *Gene VI* (Oxford University Press, Oxford, 1997).

* cited by examiner

*Primary Examiner*—Andrew Wang
*Assistant Examiner*—Jane Zara
(74) *Attorney, Agent, or Firm*—McDermott, Will & Emery (57) ABSTRACT

The present invention comprises artificial nucleic acid constructs comprising a bidirectional promoter having minimal promoter and a common promoter, wherein said minimal promoters is operably linked to said common promoter, in opposite orientation to said common promoter, and 5' to said common promoter. Those artificial nucleic acid constructs, wherein said bidirectional promoter further comprises at least one gene operably linked to said minimal promoter and said common promoter are preferred.

12 Claims, 6 Drawing Sheets

SEQUENCE LISTING

<160> NUMBER OF SEQ ID NOS: 12

<210> SEQ ID NO 1
<211> LENGTH: 30
<212> TYPE: DNA
<213> ORGANISM: synthetic construct

<400> SEQUENCE: 1
gaagatctga tatcaagctt cgcaagaccc                30

<210> SEQ ID NO 2
<211> LENGTH: 35
<212> TYPE: DNA
<213> ORGANISM: synthetic construct -continued

<400> SEQUENCE: 2
ggaattccat ggatcccggg tgtaattgta aatag                          35

<210> SEQ ID NO 3
<211> LENGTH: 30
<212> TYPE: DNA
<213> ORGANISM: synthetic construct

<400> SEQUENCE: 3
ggaagatctg aattcgtgca tccgctttgc                                30

<210> SEQ ID NO 4
<211> LENGTH: 33
<212> TYPE: DNA
<213> ORGANISM: synthetic construct

<400> SEQUENCE: 4
cccgggatcc atgaaacat attacaagac tcg                             33

<210> SEQ ID NO 5
<211> LENGTH: 42
<212> TYPE: DNA
<213> ORGANISM: synthetic construct

<400> SEQUENCE: 5
actagtagat cttacgtact acaagaaaaa taaacatgta cg                  42

<210> SEQ ID NO 6
<211> LENGTH: 70
<212> TYPE: DNA
<213> ORGANISM: synthetic construct

<400> SEQUENCE: 6
cccgggatcc atggtggaag tatttgaaag aaaattaaaa ataaaaagga aagttaaatg   60
acttttgctc                                                         70

<210> SEQ ID NO 7
<211> LENGTH: 27
<212> TYPE: DNA
<213> ORGANISM: synthetic construct

<400> SEQUENCE: 7
ttccatggct tttgtaaaaa actgttg                                   27

<210> SEQ ID NO 8
<211> LENGTH: 48
<212> TYPE: DNA
<213> ORGANISM: synthetic construct

<400> SEQUENCE: 8
ggactagtga atatatat attcagatct aggaaggaac aaagaaag               48

<210> SEQ ID NO 9
<211> LENGTH: 157
<212> TYPE: DNA
<213> ORGANISM: synthetic construct

<400> SEQUENCE: 9
agatctgata tcaagcttcg caagaccctt cctctatata aggaagttca tttcatttgg   60
agaggacagg cttcttgaga tccttcaaca attaccaaca acaacaaaca acaaacaaca  120

-continued

```
ttacaattac tatttacaat acacccggga tccatgg                                    157

<210> SEQ ID NO 10
<211> LENGTH: 134
<212> TYPE: DNA
<213> ORGANISM: synthetic construct

<400> SEQUENCE: 10
gaattcgata tcgtgcatcc gctttgccta taaataagtt ttagtttgta ttgatcgaca    60
cgatcgagaa gacacggcca tttggacgat catttgagag tctaaaagaa cgagtcttgt   120
aatatgtttc catg                                                     134

<210> SEQ ID NO 11
<211> LENGTH: 613
<212> TYPE: DNA
<213> ORGANISM: synthetic construct

<400> SEQUENCE: 11
agatcttacg tactacaaga aaaataaaca tgtacgtaac tacgtatcag catgtaaaag    60
tatttttttc caaataattt atactcatga tagattttt tttttgaaa tgtcaattaa    120 aaatgctttc ttaaatatta attttaatta attaaataag gaaatatatt tatgcaaaac   180
atcatcaaca catatccaac ttcgaaaatc tctatagtac acaagtagag aaaataaatt   240
ttactagata caaacttcct aatcatcaat tataaatgtt tacaaaacta attaaaccca   300
ccactaaaat taactaaaaa tccgagcaaa gtgagtgaac aagacttgat ttcaggttga   360
tgtaggacta aaatggctac gtatcaaaca tcaacgatca tttagttatg tatgaatgaa   420
tgtagtcatt acttgtaaaa caaaaatgct ttgatttgga tcaatcactt catgtgaaca   480
ttagcaatta catcaacctt attttcacta taaaaccca tctcagtacc cttctgaagt   540
aatcaaatta agagcaaaag tcatttaact ttcctttta tttttaattt tctttcaaat   600
acttccacca tgg                                                     613

<210> SEQ ID NO 12
<211> LENGTH: 317
<212> TYPE: DNA
<213> ORGANISM: synthetic construct

<400> SEQUENCE: 12
agatctagga aggaacaaag aaaggaatat aggttaagtt caaagtggtt aagctctcta    60
atgtcgtcaa tgaatacgtc atcatgaaga aataaataat ttccaagtgg atggacttgg   120
ggaggtccac acatacgtcg tcaatgacga ccacgtccct taaggcgaaa taaacacttg   180
ccttcctaaa ttctctgatc aatcaatgtg tataaatatg cgcagatata tccattatcc   240
tccacaattc agggaaaatc ttcaaagtgt ttgcagagaa atctaaattc atcaacagtt   300
ttttacaaaa gccatgg                                                 317
```

BIDIRECTIONAL PROMOTERS AND METHODS RELATED THERETO

FIELD OF THE INVENTION

The vast majority of promoters in plants are unidirectional, with one upstream (5') promoter directing only one gene which is 3' to the promoter. It is often desirable to introduce multiple genes into plants for metabolic engineering, trait stacking and other purposes. It is also desirable to minimize repeated use of a single promoter, because repeated use may result in gene silencing. The present invention provides a strategy to make polar promoters bidirectional so that one promoter can direct the expression of two genes.

Common promoters are polar; that is, only one gene operably linked to a promoter can be expressed. In the present invention, in contrast, the inventors have found that a naturally-occurring unidirectional promoter can be bidirectionalized by fusing a minimal promoter at its 5' end in an opposite orientation to the promoter (FIGS. 2 and 3), and that the engineered promoter can simultaneously direct the expression of two genes, with one gene on each end.

BACKGROUND OF THE INVENTION

Figure 1:
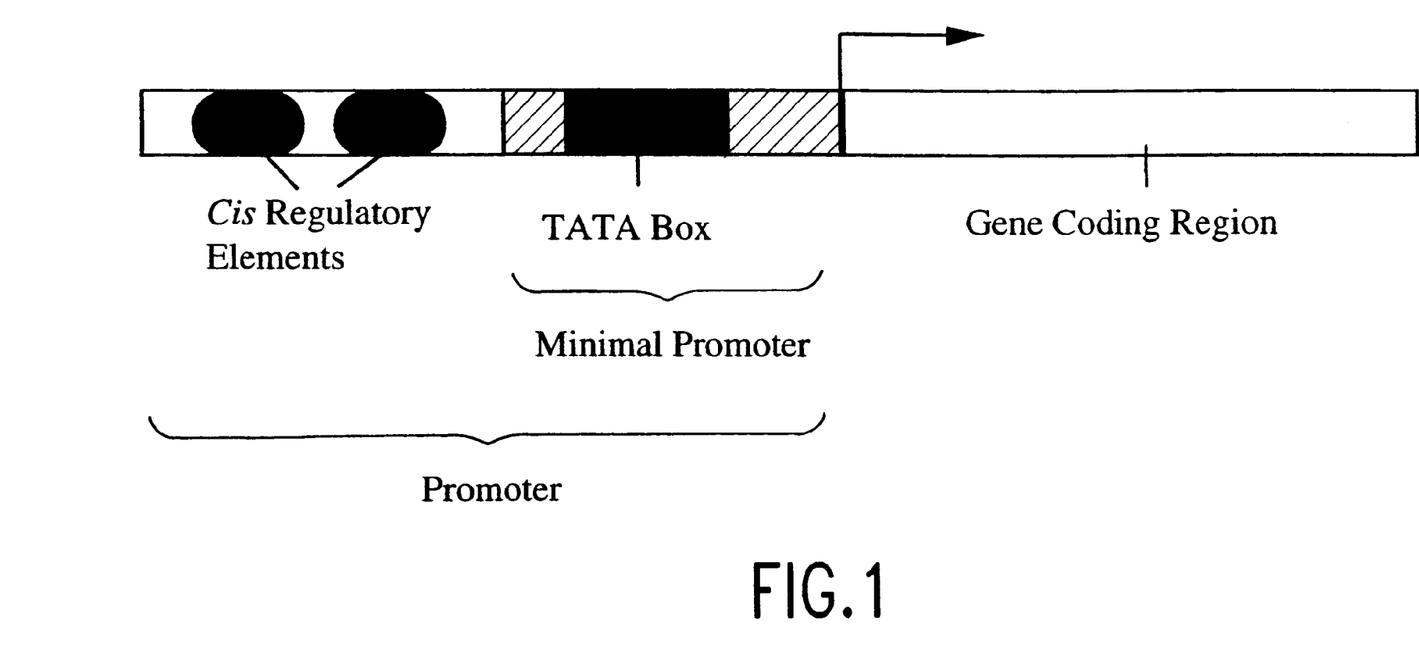
FIG. 1 is an illustration of a typical eukaryotic gene promoter (common promoter) that consists of a minimal promoter and cis regulatory elements. The arrow indicates the transcription polarity.

Gene expression consists of two major consecutive processes called transcription (from DNA to mRNA) and translation (from mRNA to protein/peptide). Transcription is often directed by a specific DNA sequence called a promoter that is in the upstream region of the transcribed DNA or gene. An eukaryotic promoter consists of two parts: one is called the core or minimal promoter, and the other comprises regulatory sequences or cis regulatory elements (FIG. 1). A minimal promoter is the DNA sequence that is immediately in the upstream of the transcription start site, and it generally contains a short sequence called the TATA box (FIG. 1). The role of a minimal promoter or TATA box is to provide a site for assembling the transcription initiation complex consisting of RNA polymerase II, transcription factor II B (TFIIB), TFIID, TFIIE, and TFIIH. However, the minimal promoter itself has no transcriptional activity. Its activation requires the cis regulatory elements on which other specific transcription factor(s) bind and subsequently interact with the transcription initiation complex to activate gene transcription. The arrangement of cis regulatory elements-minimal promoter determines that a promoter must be polar or unidirectional. Almost all eukaryotic promoters are unidirectional with one promoter directing one gene expression.

An array of promoters have been cloned and widely used for basic research and biotechnological applications. However, it is often needed to introduce multiple genes into plants for metabolic engineering and other purposes. To minimize or avoid repeated use of a single promoter (therefore minimize the potential for gene silencing), several strategies have been developed, including sequential transformation using multiple constructs with different selectable markers, co-transformation with multiple constructs, genetic crosses between plants transformed with different constructs, and fusion of multiple peptides with a plant virus proteinase-based protein splicing mechanism. The present inventors have invented a method as described below by which one can make one polar promoter bidirectional so that one promoter can be used to direct the expression of two genes, or gene fusions.

A typical eukaryotic promoter consists of a minimal promoter and other upstream cis elements. Lewin, B. Gene VI (Oxford University Press, Oxford, 1997), Odell, J. T., Nagy, F. & Chua, N.-H. Nature 313, 810–812 (1990), and Benfey, P. N. & Chua, N.-H. Science 250, 959–966 (1990). The minimal promoter is essentially a TATA box region where RNA polymerase II binds to initiate transcription, but itself has no transcriptional activity Benfey, P. N. & Chua, N.-H. Science 250, 959–966 (1990). The cis elements, upon binding by specific transcriptional factors, individually or in combination, determine the spatio-temporal expression pattern of a promoter. Benfey, P. N. & Chua, N.-H. Science 250, 959–966 (1990).

Artificial constructs as well as exception to nature's rule have been disclosed previous to the present invention. None have described a bidirectional promoter as is described herein. Representative patents are summarized below.

U.S. Pat. No. 5,814,618 discloses a bidirectional promoter which has multiple tet operator sequences (defined in the specification as enhancers or repressors) and flanking minimal promoters. U.S. Pat. No. 5,955,646 discloses bidirectional heterologous constructs. U.S. Pat. No. 5,368,855 discloses a naturally-occurring bidirectional promoter. U.S. Pat. No. 5,359,142 discloses constructs which have been manipulated to permit variation in enhancement of gene expression. U.S. Pat. No. 5627046 discloses a naturally-occurring bidirectional promoter. U.S. Pat. No. 5,827,693 discloses modified hemoglobin promoters. Significant in this patent is column 12 of the background of the invention, wherein a long list of promoters, some of which are bidirectional, are disclosed. The yeast promoters disclosed are all naturally-occurring ones.

Despite the existence of naturally-occurring bidirectional promoters, it was not clear at the time of the present invention, that any unidirectional promoter can be bidirectionalized. The U.S. Pat. No. 5,814,618 showed that seven repeats of the prokaryotic Tet repressor/operator/inducer sequences, when flanked by two minimal promoters in the presence of tetracyclin inducer, could direct the expression of two genes in eukaryotic cells where raltaed additional prokaryotic proteins/peptides were also expressed. U.S. Pat. No. 5814618 did not teach how to make an eukaryotic polar promoter bidirectional, especially when the specific sequences of the cis elements in an eukaryotic promoter were unknown. In contrast, the current invention describes a novel method by which any eukaryotic polar promoter can be bidirectionalized even at the time when the specific cis elements on the promoter may be not necessarily identified yet. There is ample art to show that stearic hindrance, and other physical as well as chemical barriers makes promoter construction unpredictable.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

In the present invention, the inventors have developed a strategy by which a naturally-occurring unidirectional promoter can be bidirectionalized by fusing a minimal promoter at its 5' end in an opposite orientation to the promoter (FIG. 1), and that the engineered promoter can simultaneously direct the expression of two genes, with one gene on each end.

The present invention comprises artificial nucleic acid constructs comprising a bidirectional promoter having minimal promoter and a common promoter, wherein said minimal promoter is operably linked 5' to the common promoter, and in opposite orientation to said common promoter. Those artificial nucleic acid constructs, wherein said bidirectional promoter further comprises at least one gene operably linked to said minimal promoters and said common promoter are preferred. In particular, those constructs wherein said minimal promoter is a minimal promoter of a promoter selected from the group consisting of cauliflower mosaic virus 35S RNA promoter (herein 35S), peanut chloritic streak caulimovirus full-length transcript promoter (herein PClSV), the Arabidopsis 12-oxophytodienoic acid-10, 11-reductase gene promoter (herein OPR), and SAG12 are preferred. The common promoter may or may not be defined or known although preferred are artificial nucleic acids comprising common promoter selected from the group consisting of cauliflower mosaic virus 35S RNA promoter (herein 35S), peanut chloritic streak caulimovirus full-length transcript promoter (herein PClSV), the Arabidopsis 12-oxophytodienoic acid-10, 11-reductase gene promoter (herein OPR), and SAG12.

In additional embodiments are artificial nucleic acid constructs which comprise at least one gene and wherein the gene is an agronomically-significant gene. In those embodiments, it is preferred that said agronomically-significant gene is selected from the group consisting of: male sterility; self-incompatibility; foreign organism resistance; improved biosynthetic pathways; environmental tolerance; photosynthetic pathways; and nutrient content and/or fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Plants comprising the nucleic acid constructs are provided, including, preferably plants selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive.

Plant parts comprising a nucleic acid constructs are also provided, particularly those selected from the group consisting of cells, seeds, embryos, leaves, roots, and stems.

The present invention also provides methods to transfer nucleic acid into a plant cell, comprising contacting a nucleic acid constructs of the present invention to at least one plant cell under conditions sufficient to allow said nucleic acid to enter said cell. In particular, there are provided methods to impart agronomically-significant characteristics to a plant, comprising contacting a nucleic acid constructs of the present invention to at least one plant cell under conditions sufficient to allow said nucleic acid to enter said cell.

By "agronomically-significant" it is meant any trait of a plant which is recognized by members of the agricultural industry as desirable.

"Common" or "unidirectional" or "polar" promoter means a naturally-occurring unidirectional promoter, or a unidirectional promoter which is an obvious variation of a naturally-occurring unidirectional promoter.

"Operatively linked" the spatial relationship of two or more pieces of DNA such that the referent piece(s) is capable of effecting an intended genetic outcome of another referent sequence. The pieces may be joined together by recombinant DNA techniques, including, but not limited to, restriction enzyme digestion and ligations.

By "plant" it is meant one or more plant seed, plant embryo, plant part or whole plant. The plant may be an angiosperm (monocot or dicot), gymnosperm, man-made or naturally-occurring.

By "proteins" it is meant any compounds which comprise amino acids, including peptides, polypeptides, fusion proteins, etc.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

BRIEF DESCRIPTION OF THE DRAWINGS

FIG. 5 shows typical examples of GUS stainings in transgenic Arabidopsis thaliana (ecotype gl1) seedlings (25-day old) transformed with (A) pGL429 or (B) pGL489.

DETAILED DESCRIPTION OF THE INVENTION

The present invention comprises artificial nucleic acid constructs comprising a bidirectional promoter having minimal promoter and a common promoter, wherein said minimal promoter is operably linked 5' to the common promoter, and in opposite orientation to said common promoter. Those artificial nucleic acid constructs, wherein said bidirectional promoter further comprises at least one gene operably linked to said minimal promoters and said common promoter are preferred. In particular, those constructs wherein said minimal promoter is a minimal promoter of a promoter selected from the group consisting of cauliflower mosaic virus 35S RNA promoter (35S), peanut chloritic streak caulimovirus full-length transcript promoter (PClSV), the Arabidopsis 12-oxophytodienoic acid-10, 11-reductase gene promoter (OPR), and SAG12 are preferred. The common promoter may or may not be fully defined scientifically (may be identified, but not fully characterized). Preferred are artificial nucleic acids comprising common promoter selected from the group consisting of cauliflower mosaic virus 35S RNA promoter (35S), peanut chloritic streak caulimovirus full-length transcript promoter (PClSV), the Arabidopsis 12-oxophytodienoic acid-10, 11-reductase gene promoter (OPR), and SAG12.

In additional embodiments are artificial nucleic acid constructs which comprise at least one gene and wherein the gene is an agronomically-significant gene. In those embodiments, it is preferred that said agronomically-significant gene is selected from the group consisting of: male sterility; self-incompatibility; foreign organism resistance; improved biosynthetic pathways; environmental tolerance; photosynthetic pathways; and nutrient content and/or fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Plants comprising the present constructs are provided, including, preferably plants selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive.

Plant parts comprising a constructs of the present invention are also provided, particularly those selected from the group consisting of cells, seeds, embryos, leaves, roots, and stems.

The present invention also provides methods to transfer nucleic acid into a plant cell, comprising contacting a nucleic acid constructs of the present invention to at least one plant cell under conditions sufficient to allow said nucleic acid to enter said cell. In particular, there are provided methods to impart agronomically-significant characteristics to a plant, comprising contacting a nucleic acid constructs of the present invention to at least one plant cell under conditions sufficient to allow said nucleic acid to enter said cell.

The present invention also comprises a method of bidirectionalizing promoters so that one promoter can be used to direct the expression of two genes. Briefly, the method involves fusing a minimal promoter (essentially a TATA box-like region) to the 5' end of a regular promoter in an opposite direction; then two genes of interest with appropriate 3' terminators can be fused to the ends of the reconstructed promoter, with one gene on each end.

Figure 2:
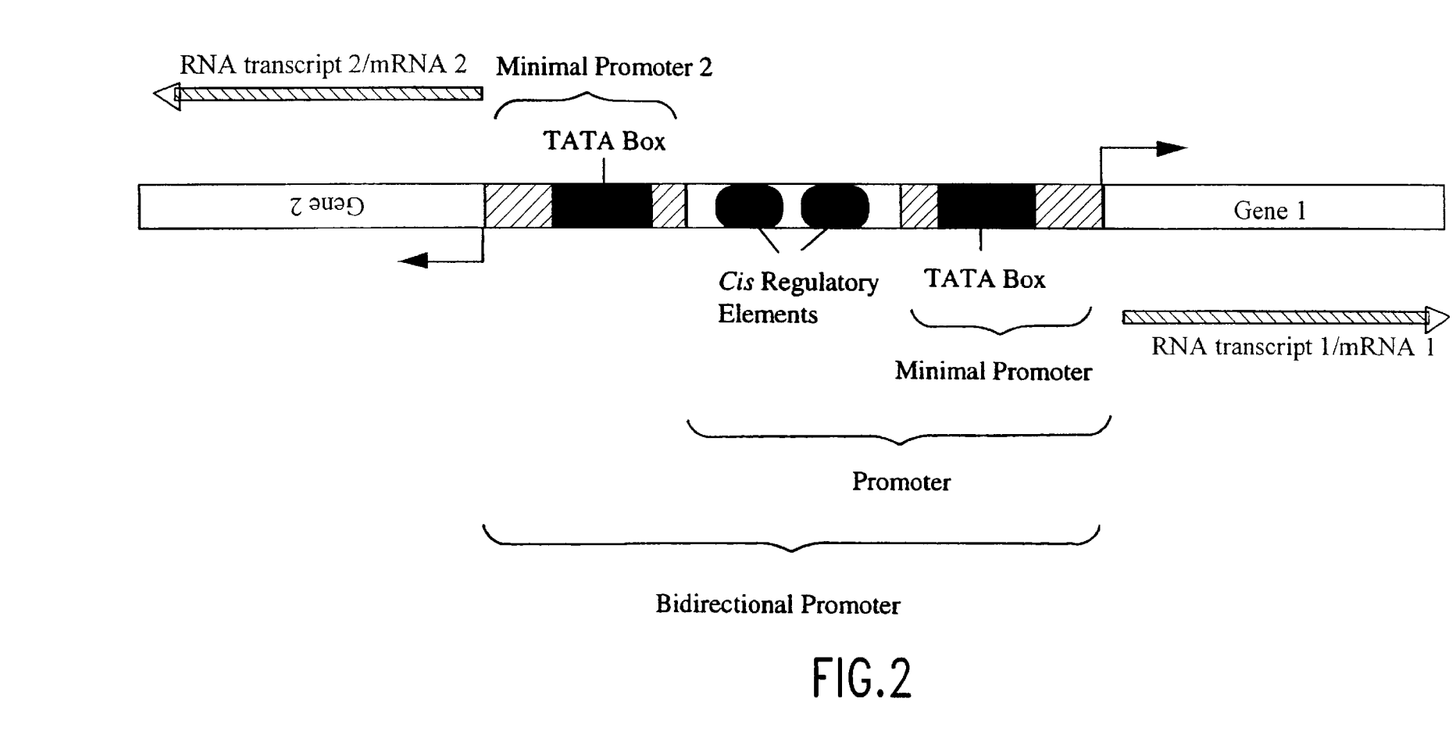
FIG. 2 is an illustration of the novel strategy for bidirectionalizing a typical eukaryotic gene promoter by fusing a minimal promoter at the 5' end of the promoter in opposite orientation. The minimal promoter can be the same as that of the common promoter (homogeneous) or derived from a different eukaryotic promoter (heterogenetic).
Figure 3:
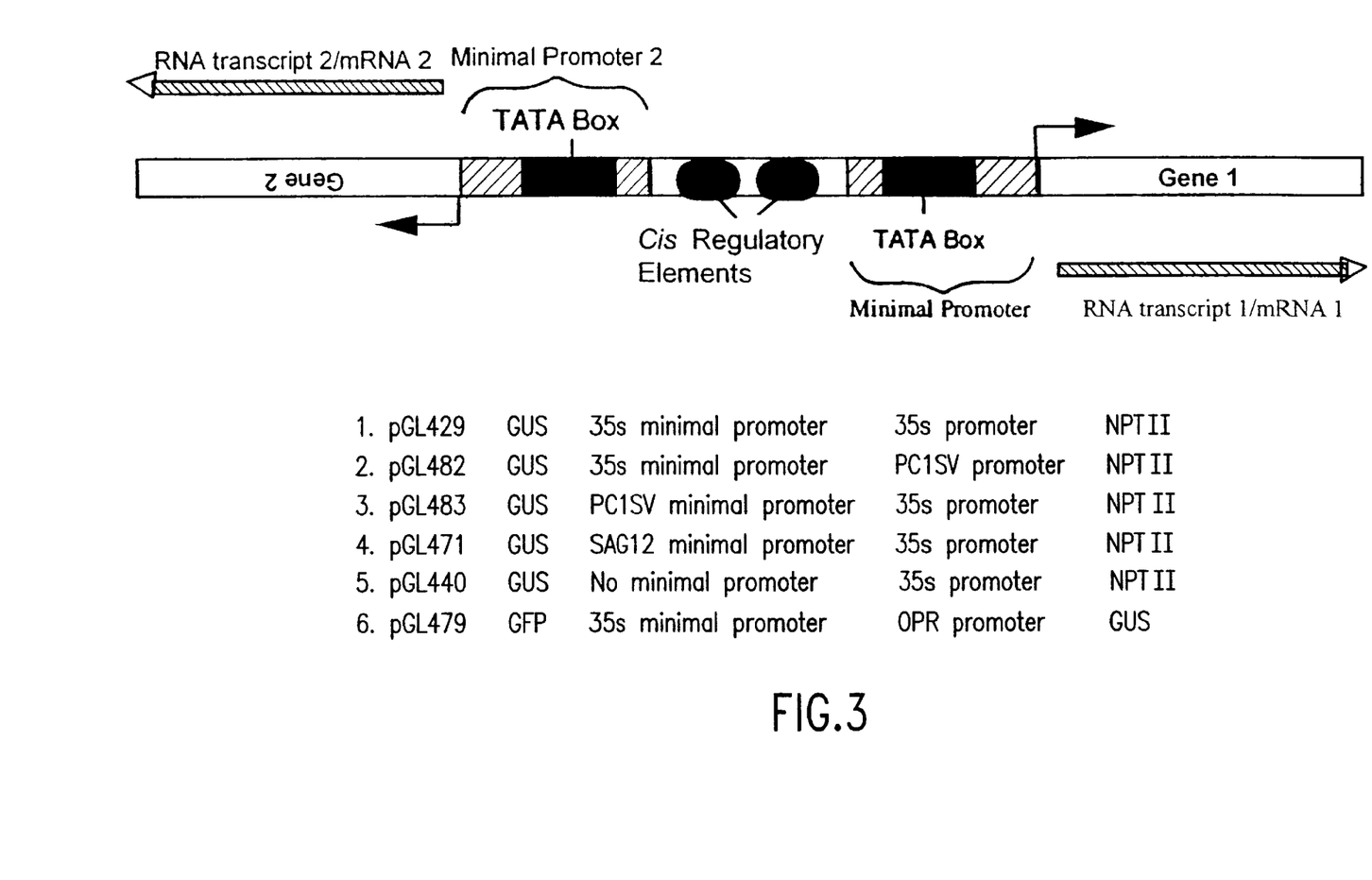
FIG. 3 is a diagram of promoter bidirectionalization strategy and some constructs. A common promoter directing the gene 1 expression can be bipolarized by fusing a minimal promoter at its 5' end in an opposite orientation so that it can also direct the gene 2 expression. 1 to 6 are different constructs in the pPZP211 vector. NPT II encodes an enzyme that renders a transgenic plant resistant to kanamycin mini stands for minimal promoter. PClSV is the peanut chlorotic streak virus full-length transcript promoter. SAG-mini is a minimal promoter derived from the senescence-specific SAG12 promoter. OPR1 is an inducible promoter. GUS (β-glucuronidase) and GFP (green fluorescent protein) are reporter genes.

In one embodiment is a method that involves fusing a minimal promoter at the 5' end of a promoter (FIG. 2). The orientation of the minimal promoter is opposite to the regular promoter. The recombinant promoter then becomes bidirectional. After genes of interest are operably linked to the recombinant promoter with one gene at each end of the recombinant promoter (FIG. 2), the construct will direct the expression of both genes simultaneously in transgenic plant cells.

Figure 5A:
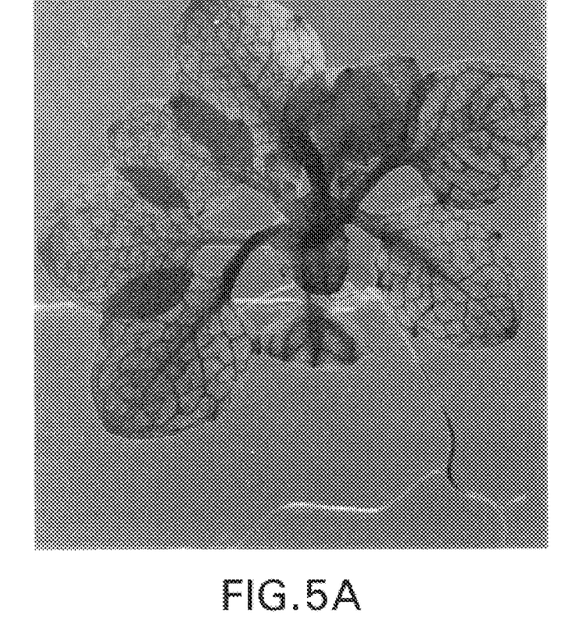
Figure 5B:
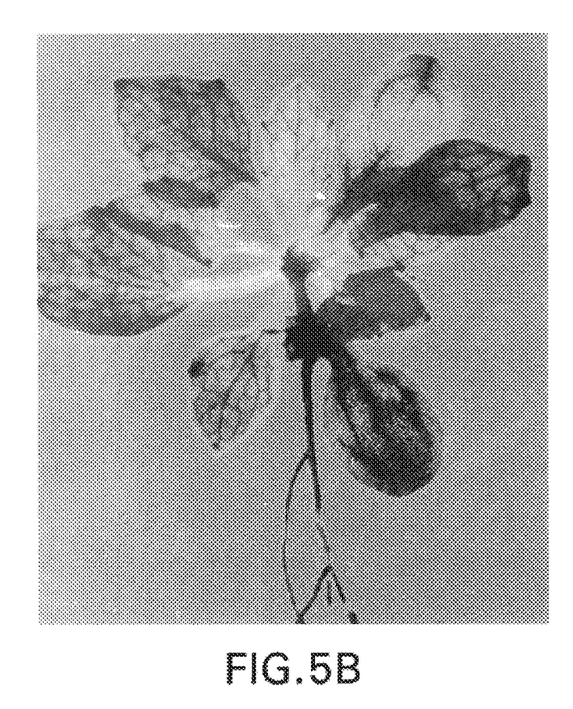
Figure 6:
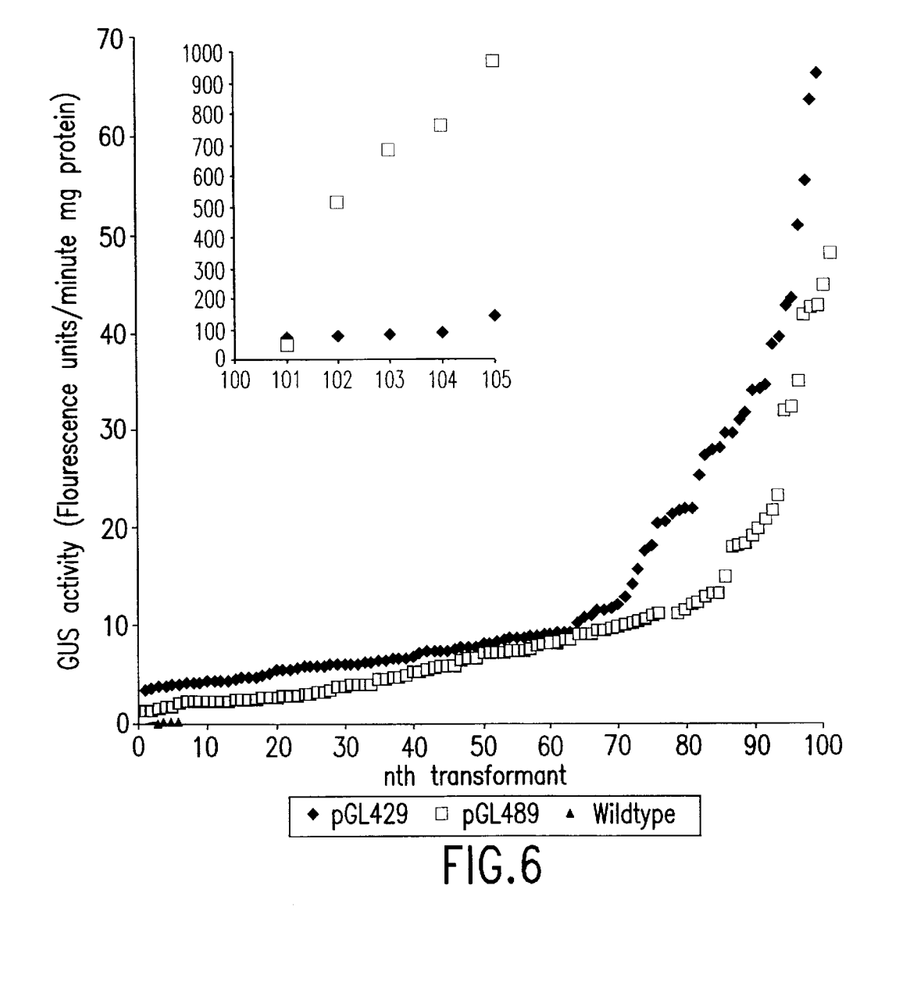
FIG. 6 shows the GUS expression levels in randomly selected 105 T1 Arabidopsis seedlings (excluding roots) transformed with pGL429 (♦) or pGL489 (■). The background value for 4 nontransgenic wild-type plants is also presented (▼).

The inventors made various constructs (FIG. 3) and demonstrated that the constitutive promoters such as cauliflower mosaic virus (CaMV) 35S promoter or peanut chlorotic streak caulimovirus (PClSV) full-length transcript (FLt) promoter, upon being bidirectionalized (constructs 1–4 in FIG. 3), can efficiently direct the expression of two genes that have been fused at the respective ends of the engineered promoter regardless the source of the minimal promoter. The constitutive expression pattern of both genes appears to be similar (if not identical) to each other. FIG. 5A shows a typical GUS expression pattern directed by the 35S minimal promoter-bidirectionalized 35S promoter compared with (in 5B) the expression pattern directed by the common 35S promoter. The expression level of each gene from the bidirectional promoter appears to be comparable to that from unidirectional promoter. The GUS expression levels directed by the 35S minimal promoter-bidirectionalized 35S promoter in 100 out of 105 randomly selected transgeneic Arabidopsis seedlings are indeed even higher than those directed by the 35S promoter (FIG. 6). There were four plants in which 35S promoter-directed GUS expression was higher than that directed by bidirectionalized promoter (FIG. 6 insert). This could result from the position effect because the 35S promoter directing the GUS expression in pGL489 was adjacent to the right border of T-DNA. However, there is essentially no expression of the second gene if a second minimal promoter is not present (PGL 440 in FIG. 3); the fusion of a minimal promoter at the 5' end of a promoter makes the promoter become bidirectional. The bidirectionalized promoters are heritable in the first three generations so far tested.

As mentioned above, a minimal promoter is essential for bidirectionalizing a promoter. The minimal promoter could be derived from the promoter that was to be bidirectionalized (e.g., the constitutive expression cauliflower mosaic virus or CaMV 35S promoter and its minimal promoter in pGL429). The minimal promoter could also be derived from other promoters than the promoter that was to be bidirectionalized, e.g., the minimal promoter in pGL483 was derived from the peanut chlorotic streak virus or PClSV promoter (a constitutive expression promoter), and the minimal promoter in pGL471 was derived from the SAG12 promoter (a senescence-specific promoter). The minimal promoter is essentially a TATA box region where the RNA polymerase II and other factors bind to initiate transcription in eukaryotes). The minimal promoter itself has no transcriptional activity. As expected, the different minimal promoters used here just functioned the same; all of them bidirectionalized the 35S promoter. The effectiveness of the heterologous source of minimal promoter was also demonstrated in pGL482 and pGL479, in which the 35S minimal promoter was able to bidirectionalize the PClSV promoter (a constitutive expression promoter) and the 12-oxo-phytodienoic acid reductase (OPR1) promoter, respectively. The OPR1 promoter is a jasmonate-, wound-, and senescence-inducible promoter, thus demonstrating that inducible promoters can also be bidirectionalized, in addition to the constitutive 35S and PClSV promoters.

The number of base pairs between the minimal promoters and the regular promoters in the examples are as follows, although the number of base pairs between the minimal promoter and common promoter is not as important as the need to be operably linked:

pGL429: 261bp (−51 of the 35S minimal promoter to ~746 of the 35S promoter) (SEQ ID NO. 9); these are pPZP211 vector sequences.

pGL482: 30bp (−51 of the 35S minimal promoter to 5' end of the PClSV promoter) (SEQ ID NO. 9); these are pPZP211 vector multiple cloning site sequences.

pGL483: 240bp (5' end of the PClSV minimal promoter to ~746 of the 35S promoter) (SEQ ID NO. 10); these are pPZP211 vector sequences.

pGL471: 277bp (−469 of the SAG12 minimal promoter to ~746 of the 35S promoter) (SEQ ID NO. 11); these are pPZP211 vector sequences.

pGL479: 12bp (−51 of the 35S minimal promoter to ~246 of the OPR1 promoter) (SEQ ID NO.12); these are pPZP211 vector sequences.

pGL440: 267bp (from the translation start codon ATG of the GUS ORF to ~746 of the 35S promoter); these are pPZP211 vector sequences.

The TATA box region and cis elements of the 35S promoter have been described (Benfey, P. N. & Chua, N.-H. Science 250, 959–966 (1990). The PClSV promoter has also been described (Maiti, I. B. & Shepherd, R. J. Biochem Biophys Res Commu 244,440–44 (1998). The SAG12 minimal promoter was found no transcriptional activity (Gan, S. & Amasino, R. M. Science 270, 1986–1988 (1995). The OPR1 promoter sequence was also reported. (Biesgen, C. & Weiler, E. W. Planta 208, 155–165 (1999).

The inventors first tested the widely used cauliflower mosaic virus 35S promoter. The 35S minimal promoter (−51 to transcription start point), when fused at the 5' end of the regular 35S promoter (−746 to start point), was able to constitutively direct the reporter gene (β-glucuronidase (GUS) expression in all 150 independent transgenic Arabidopsis lines that were resistant to kanamycin (50 µg ml$^{-1}$) conferred by the 35S promoter directed NPT II gene (pGL429 in FIG. 3) (FIG. 5). The GUS expression level in each line varies (FIG. 6). The minimal promoter is necessary for bidirectionalizing the promoter because transgenic Arabidopsis plants harboring a similar construct without the minimal promoter (pGL440 in FIG. 3) did not show GUS expression.

The inventors then investigated if a heterogenetic minimal promoter can also bipolarize the 35S promoter. When the minimal promoters derived from the peanut chlorotic streak virus (PClSV) promoter or from the senescence-specific SAG12 promoter replaced the 35S minimal promoter in pGL429 to form pGL483 and pGL471, respectively, transgenic plants harboring these constructs (47 and 22 independent plants for respective constructs) all showed constitutive GUS expression.

The ability of this bidirectionalization strategy was also demonstrated using another constitutive expression promoter, the PClSV promoter. The 364 base pairs PClSV promoter was used to direct the NPT II for kanamycin resistance in transgenic plants. When a 35S minimal promoter-GUS-mas terminator was fused at the 5' end of the promoter (pGL482 in FIG. 3), the PClSV promoter was able to direct the GUS expression in all 29 kanamycin-resistant Arabidopsis plants.

In addition to the constitutive 35S and PClSV promoters, the inventors found that the OPR1 promoter, an inducible promoter by wounding, jasmonate and senescence, was bidirectionalized by the 35S minimal promoter (pGL479 in FIG. 3) in all 8 lines of transgenic Arabidopsis plants we obtained. Both the GUS and the green fluorescent protein (GFP) expression was detected in senescing leaves and induced by wounding and jasmonate treatment in young leaves.

The heritability and stability of the bidirectionalized promoters was examined in randomly selected 10 independent Arabidopsis lines transformed with pGL429. All progeny (the second and third generations) of these lines that were resistant to kanamycin showed constitutive GUS expression.

Vectors which comprise the above constructs are within the scope of the present invention, as are plants transformed with the above constructs. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Preferred vectors are those binary vectors which are capable of transferring the sequences disclosed herein into plant cells or plant parts. Examples of the binary vectors the inventors used are those pPZP100s and pPZP200s series vectors (Hajdukiewiscz, P., Svab,Z. & Maliga, P. (1994) The small, versatile pPZP family of Agrobacterium binary vectors for plant transformation. Plant Molecular Biology 25: 989–994).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein may be improved by fragmenting, modifying, or derivatizing nucleic acid molecules encoding such a protein.

Constructs of the present invention may be transferred to cells according to the methods of the present invention, as well as using any of the following well-known means: infective, vector-containing bacterial strains (such as Agrobacterium rhizogenes and Agrobacterium tumefaciens) according to e.g. Zambryski, 43 Ann. Rev. Pl . Physiol. Pl. Mol Biol 465 (1992); pollen-tube transformation [Zhon-xun et al., 6 Plant Molec. Bio. 165 (1988)]; direct transformation of germinating seeds [Toepfer et al., 1 Plant Cell 133 (1989)]; polyethylene glycol or electroporation transformation [Christou et al., 84 Proc. Nat. Acad. Sci 3662 (1987)]; and biolistic processes [Yang & Christou, Particle Bombardment Technology for Gene Transfer (1994)].

The transformed cells may be induced to form transformed plants via organogenesis or embryogenesis, according to the procedures of Dixon Plant Cell Culture: A Practical Approach (IRL Press, Oxford 1987).

EXAMPLES

Reactions and manipulations involving DNA techniques, unless stated otherwise, were performed as described in Sambrook et al., 1989, Molecular Cloning: A Laboratory Manual, Cold Spring Harbor Laboratory Press.

Constructs

Figure 4:
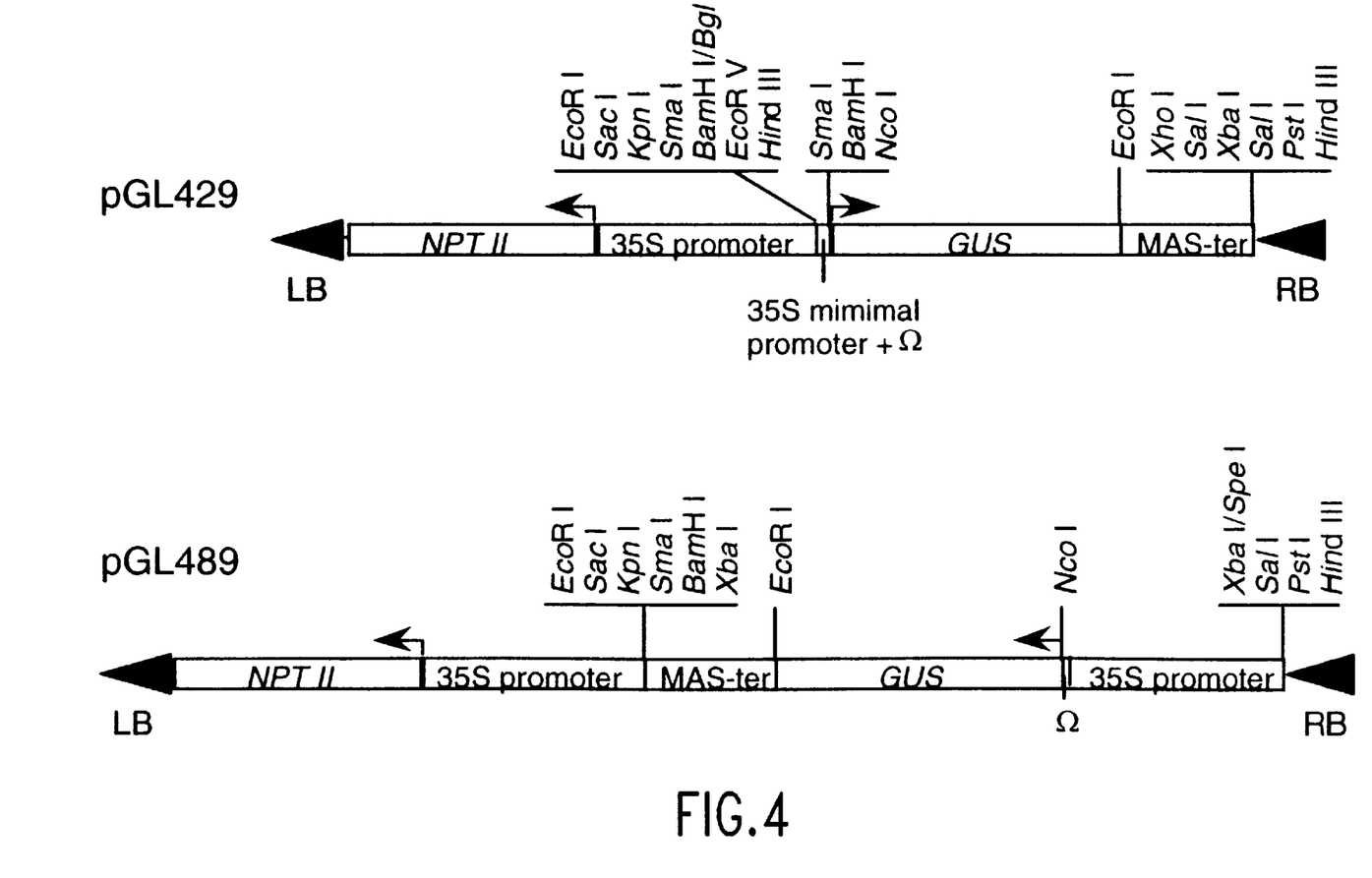
FIG. 4 are schematic maps of pGL429 (where the bidirectionalized CaMV 35S promoter directs the expression of the reporter gene GUS) and pGL489 (where the common 35S promoter controls the GUS expression. BamH I/Bgl II in pGL429 and Xba I/Spe I in pGL489 are two compatible restriction enzyme sites that are ligated. LB and RB are the left and right T-DNA border. Small arrows indicate the transcriptional start site and polarity.

Standard DNA manipulation (restriction digestion, plasmid isolation, cloning, etc.) was performed as described in Sambrook, J., E. F. Fritsch, et al. (1989). Molecular Cloning: A Laboratory Manual. New York, Cold Spring Harbor Laboratory Press.

pGL429: the CaMV 35S minimal promoter (−51 region) with the TMV RNA (leader sequence was PCR-amplified using pSH9 (Holtorf, S., K. Apel, et al. (1995). Comparison of different constitutive and inducible promoters for the overexpression of transgenes in Arabidopsis thaliana. Plant Mol. Biol. 29: 637–646) as the template with two primers (5'GAAGATCTGATATCAAGCTTCGCAAGACCC3' (SEQ ID NO:1) and 5'GGAATTCCATGGATCCCGGGTG-TAATTGTAAATAG3' (SEQ ID NO:2)). The omega leader sequence can enhance gene expression at the posttranscriptional level (Gallie, D. R., D. E. Sleat, et al. (1987). The 5'-leader sequence of tobacco mosaic virus RNA enhances the expression of foreign gene transcripts in vitro and in vivo. Nucleic Acids Res 15: 3257–3273). The PCR product, upon cut with Bgl II and EcoR I, was cloned into pLIT-MUS28 (New England Biolab, Mass., USA) to form pGL400. A GUS-MAS terminator from pSG506 (Gan, S. (1995). Molecular characterization and genetic manipulation of plant senescence. Department of Biochemistry. Madison, University of Wisconsin-Madison: 190) was then cloned into pGL400 at the Nco I and Xba I sites to form the 35S minimal promoter-GUS-MAS terminator (pGL407), which was subsequently cloned into the binary vector pPZP211 at the BamH I and Xba I sites to form pGL429. The 35S promoter (−419 region)-NPT II was part of the pPZP211 sequence (Hajdukiewicz, P., Z. Svab, et al. (1994). The small, versatile pPZP family of Agrobacterium binary vectors for plant transformation. Plant Mol Biol 25: 989–994).

pGL482: the 364 base pairs of peanut chlorotic streak caulimovirus (PClSV) full length transcript promoter (Maiti, I. B. and R. J. Shepherd (1998). Isolation and expression analysis of peanut chlorotic streak caulimovirus (PClSV) full-length transcript (FLt) promoter in transgenic plants. Biochemical and Biophysical Research Communications 244: 440–444.) was cloned into pPZP211 at the EcoR I and Nco I sites to form pGL455. The 35S minimal promoter-GUS-MAS terminator of pGL407 was then subcloned into pGL455 to form pGL482.

pGL483: the 117 base pairs of the PClSV minimal promoter was generated by PCR using a pair of primers (5'GGAAGATCTGAATTCGTGCATCCGCTTTGC3' (SEQ ID NO:3) and 5'CCCGGGATCCATGGAAACATAT-TACAAGACTCG3' (SEQ ID NO:4)), which was fused with the GUS-MAS terminator of pSG506 (Gan 1995). The PClSV minimal promoter-GUS-MAS terminator was then cloned into the binary vector pPZP211 at the BamH I and Xba I sites.

pGL471: using pSG499 (Gan 1995) as the template, the SAG12 minimal promoter was PCR-cloned with the following pair of primers: 5'ACTAGTAGATCTTACGTACTA-CAAGAAAAATAAACATGTACG3' (SEQ ID NO:5) and 5'CCCGGGATCCATGGTGGAAG-TATTTGAAAGAAAATTAAAAATAAAAAGGAAAG TTAAATGACTTTTGCTC3' (SEQ ID NO:6). The second primer contained the 34 bases of AMV RNA4 leader sequence that will enhance expression at the posttranscriptional level (Jobling, S. A. and L. Gehrke (1987). Enhanced translation of chimeric messenger RNAs containing a plant viral untranslated leader sequence. Nature 325: 622–625.). This minimal promoter contains 469 bp from the transcription start site, 100 bp of the SAG12 5'UTR sequence and the 34 bp of AMV RNA4 leader sequence. This minimal promoter was fused with the GUS-MAS terminator (pGL467), which was subsequently cloned into pPZP211 at the XbaI site, resulting in two types of plasmid depending on the orientation of the SAG12 minimal promoter-GUS-MAS terminator relative to the 35S promoter-NPT II on the vector. The one with an opposite orientation was named pGL471.

pGL479: in an effort to identify genes that are upregulated during leaf senescence and inducible by jasmonate using enhancer trap strategy in Arabidopsis, the inventors cloned a gene, OPR1, that encodes the 12-oxophytodienoic acid reductase. In addition to senescence and jasmonate, this gene is inducible by wounding (Biesgen, C. and E. W. Weiler (1999). Structure and regulation of OPR1 and OPR2, two closely related genes encoding 12-oxophytodienoic acid-10,11-reductases from Arabidopsis thaliana. Planta 208: 155–165.). A PCR technique is employed to clone the promoter region of the promoter (310 bp) with the Arabidopsis (ecotype Columbia) genomic DNA as the template and the following pair of primers: 5'TTCCATGGCTTTTG-TAAAAACTGTTG3' (SEQ ID NO:7) and 5'GGAC-TAGTGAATATATATATATTCAGATCTAG-GAAGGAACAAAGAAAG3' (SEQ ID NO:8). These primers introduced an Nco I site at the 3' end of the promoter and a Bgl II site at the 5' end. The PCR-amplified promoter was fused with the GUS-MAS terminator to form OPR1-GUS-MAS terminator chimeric gene in pGL332. The 35S minimal promoter (−51 region)-GFP-NOS terminator was PCR-amplified using psmGFP (Davis, S. J. and R. D. Vierstra (1998). Soluble, highly fluorescent variants of green fluorescent protein (GFP) for use in higher plants. Plant Mol. Biol. 36: 521–528.) as the template with the following two primers: one is the M13 reverse primer and the other is 5'GAAGATCTGATATCAAGCTTCGCAAGACCC3'. The PCR product was digested with both EcoR I and EcoR V, and subsequently cloned into pPZP211 at the EcoR I and Sma I sites to form pGL474. Finally, the OPR1-GUS-MAS terminator chimeric gene was released from pGL332 using the restriction enzymes Bgl II and Xba I, and subcloned into pGL474 at the BamH I and Xba I sites to form pGL479.

pGL440 was derived from a plasmid called pGL418 (similar with pGL429) by removing the 35S minimal promoter.

pGL489: the 35S promoter plus the omega sequence was released from pSH9 (Holtorf, S., Apel, K. and Bohlmann, H. (1995) Comparison of different constitutive and inducible promoter for the overexpression of transgenes in Arabidopsis thaliana. Plant Mol Biol 29: 637–646) with the restriction enzymes Hind III and Nco I, and then subcloned into pGL407 at the same restriction sites to form the chimeric gene 35S-GUS-MAS-ter in pGL488. This chimeric gene was released from pGL488 with restriction enzymes Spe I and Xba I, and subsequently cloned into the binary vector pPZP211 at the Xba I site, resulting two plasmids, the one shown in FIG. 4 was designated pGL489.

Agrobacterium transformation

The above constructs were transferred into Agrobacterium tumerfaciens strain ABI) using the freeze-thaw method (An, G. (1987). Binary Ti vectors for plant transformation and promoter analysis. Methods in Enzymology: Recombinant DNA. R. Wu and L. Grossman. San Diego, Academic Press. 153: 292–305.). Briefly, about 2–5 µg of each of the DNA constructs was added to a 1.5-ml microcentrifuge tube containing 100 µl of competent ABI cells, upon mixed, the mixer was frozen in dry ice-ethanol bath, then placed in 37° C. water bath for 5 minutes. 100 µl of YEP media was added into the tube, and the whole cells in the tube were plated on the YEP plate containing 100 µg/L spectinomycin (YEP: 10 g/L Bacto-peptone, 10 g/L Bacto-yeast extracts, 5 g NaCl; for plates, add 10 g/L phytoagar).

Plant transformation and cultivation

The Agrobacterium ABI cells containing the various constructs were used to transform Arabidopsis (ecotype Columbia) via vacuum infiltration (Bechtold, N., J. Ellis, et al. (1993). In Planta Agrobacterium-mediated gene transfer by infiltration of adult Arabidopsis plants. C. R. Acad. Sci. Paris 316: 1194–1199.). Briefly, about 200 mL YEP medium with 100 µg/L spectinomycin was inoculated with 10 mL of preculture of Agrobacterium harboring the respective construct. The cells of overnight culture (28° C., 250 RPM shaker) with ~1.4 OD600 was pelletted by centrifugation and resuspended in 200 mL of infiltration medium (½× Murashige-Skoog salts, 1× B5 vitamins, 5% sucrose, 0.5 g MES, 0.044 µM benzylaminopurine and 0.02% Silwet L-77, pH 5.7). The resuspension was transferred into a 250 mL beaker, and a pot of Arabidopsis plants that had several flowers was invertedly submerged in the cell suspension and vacuumed for 10–15 min using an air vacuum pump. The plants were allowed to complete their life cycle and the seeds were harvested. After surface-sterilized with 70% ethanol containing 0.1–0.2% Triton X-100, the seeds were sown on MS plates containing kanamycin (50 mg/L) and incubated 23° C. in an Arabidopsis growth chamber with 65% relative humidity under ~150 µmol m$^{-2}$s$^{-1}$ continuous light from a mixture of cool white fluorescent (60%) and incandescent (40%) bulbs. The transgenic seedlings were either assayed for GUS expression or transplanted into soil. The plants were grown in a plant growth facility under the conditions similar to those defined previously.

Tobacco (Nicotiana tabacum cv. Wisconsin38 or W38) transformation was performed using the standard Agrobacterium-mediated tissue culture method as described (Horsch, R. B. et al., (1985) A simple and general method for transferring genes into plants. Science 227:1229–1231). Transgenic tobacco plants were grown in a greenhouse at 23–25° C. under 16/8 light/dark cycle with 60% relative humidity.

GUS Enzyme Assays

The GUS assays in transgenic plants were performed histochemically and quantitatively according to the standard protocol (Jefferson, R. A. (1987). Assaying chimeric genes in plants: the GUS gene fusion system. Plant Mol Biol Rep 5: 387–405.). X-glucuronide was used as substrate for histochemical staining, and 4-methylumbelliferyl-β-D-gucuronide for quantitative assays.

GFP Expression Induced by Jasmonate, Wounding and Senescence

For the jasmonate induction treatment, young, nonsenescent leaves of pGL479 transgenic Arabidopsis plants were floated on 3 mM 2-[N-morpholino]-ethanesulfonic acid (MES) buffer (pH5.8) containing 30 µM (−)-jasmonic acid (naturally occurring form from Sigma) for 1–3 hours. For controls, nontransgenic leaves that were subject to the same treatment.

For wounding treatment, the young, nonsenescent leaves were wounded by pinching using a pair of forceps.

The above treated leaves and leaves at senescence stage 3 (about 50% distal part of a leaf turned yellow but the rest was still green) were examined for GFP expression using a NikonTE200 microscope. The soluble modified green fluorescent protein, smGFP, has a maximum excitation wavelength of 397 nm and an emission wavelength of 507 nm (Davis, S. J. and R. D. Vierstra (1998). Soluble, highly fluorescent variants of green fluorescent protein (GFP) for use in higher plants. Plant Mol. Biol. 36: 521–528.). After the fluorescence microscope detection of GFP, the samples were examined histochemically for GUS expression as described above.

Although the present invention has been fully described herein, it is to be noted that various changes and modifications are apparent to those skilled in the art. Such changes and modifications are to be understood as included within the scope of the present invention as defined by the appended claims.

What is claimed is:

1. An artificial nucleic acid construct, comprising a bidirectional promoter having a minimal promoter and a common promoter, each end of the bidirectional promoter operably linked to a polynucleotide coding for a polypeptide,
   (a) wherein said minimal promoter is operably linked to said common promoter, in opposite orientation to said common promoter, and 5' to said common promoter;
   (b) wherein said bidirectional promoter further comprises a bidirectional promoter feature selected from the group consisting of said minimal promoter, and said common promoter;
   (b) wherein said minimal promoter is a minimal promoter of a promoter selected from the group consisting of 35S, PClSV OPR, and SAG12; and
   (c) wherein said common promoter is selected from the group consisting of 35S, PCISV, OPR, and SAG12.

2. The artificial nucleic acid construct of claim 1, wherein said polynucleotide codes for an agronomically-significant polypeptide.

3. The artificial nucleic acid construct of claim 2, wherein said polypeptide functions in a metabolic pathway selected from the group consisting of male sterility; self-incompatibility; foreign organism resistance; improved biosynthetic pathways; environmental tolerance; photosynthetic pathways; and nutrient content.

4. The artificial nucleic acid construct of claim 2, wherein said polypeptide functions in a metabolic pathway selected from the group consisting of fruit ripening; oil biosynthesis; pigment biosynthesis, seed formation; starch metabolism; salt tolerance, cold/frost tolerance; drought tolerance; tolerance to anaerobic conditions; protein content; carbohydrate content (including sugars and starches); amino acid content; and fatty acid content.

5. A plant comprising a nucleic acid construct of claim 1.

6. The plant of claim 5, wherein said plant is selected from the group consisting of: soybean; maize; sugar cane; beet; tobacco; wheat; barley; poppy; rape; sunflower, alfalfa; sorghum; rose; carnation; gerbera; carrot; tomato; lettuce; chicory; pepper, melon; cabbage; oat; rye; cotton; flax; potato; pine; walnut; citrus (including oranges, grapefruit etc.); hemp; oak; rice; petunia; orchids; Arabidopsis; broccoli; cauliflower, brussel sprouts; onion; garlic; leek; squash; pumpkin celery; pea; bean (including various legumes); strawberries; grapes; apples; pears; peaches; banana; palm; cocoa; cucumber, pineapple; apricot; plum; sugar beet; lawn grasses, maple; triticale safflower, peanut; and olive.

7. A plant part comprising a nucleic acid construct of claim 1.

8. The plant part of claim 7, wherein said plant part is selected from the group consisting of cells, seeds, embryos, leaves, roots, and stems.

9. A method to transfer nucleic acid into a plant cell, comprising contacting a nucleic acid construct of claim 1 to at least one plant cell under conditions sufficient to allow said nucleic acid to enter said cell.

10. A method to impart agronomically-significant characteristics to a plant, comprising contacting a nucleic acid construct of claim 1 to at least one plant cell under conditions sufficient to allow said nucleic acid to enter said cell.

11. A method of making a bidirectional promoter for use in plants, comprising
  (1) obtaining a polynucleotide comprising a plant promoter, wherein the plant promoter comprises a Common promoter region selected from the group consisting 35S, PCISV, OPR and SAG 12;
  (2) linking a minimal promoter, selected from the group consisting of 35S, PCISV, OPR and SAG12, and the common promoter to provide a recombinant polynucleotide, such that the recombinant polynucleotide comprises the common promoter operably linked with the minimal promoter, wherein
    (a) the minimal promoter is in opposite orientation to said common promoter, and;
    (b) the minimal promoter is 5' to said common promoter.

12. The method of claim 11, wherein said bidirectional promoter further comprises a first gene operably linked to said minimal promoter and a second gene operably linked to said common promoter, and wherein said first and second genes are optionally the same gene.

* * * * *